(12) United States Patent
Jang et al.

(10) Patent No.: US 12,396,749 B2
(45) Date of Patent: Aug. 26, 2025

(54) MAGNETIC CATHETER

(71) Applicant: IUCF-HYU (INDUSTRY-UNIVERSITY COOPERATION FOUNDATION HANYANG UNIVERSITY), Seoul (KR)

(72) Inventors: Gun Hee Jang, Seoul (KR); Eun Soo Jung, Seoul (KR); Na Hyun Kim, Busan (KR); Ji Min Park, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 475 days.

(21) Appl. No.: 17/796,450

(22) PCT Filed: Dec. 30, 2020

(86) PCT No.: PCT/KR2020/019447
§ 371 (c)(1),
(2) Date: Jul. 29, 2022

(87) PCT Pub. No.: WO2021/153917
PCT Pub. Date: Aug. 5, 2021

(65) Prior Publication Data
US 2023/0338056 A1   Oct. 26, 2023

(30) Foreign Application Priority Data
Jan. 31, 2020 (KR) .......... 10-2020-0011472
Jun. 12, 2020 (KR) .......... 10-2020-0071852

(51) Int. Cl.
A61B 17/3207   (2006.01)
A61B 17/00     (2006.01)
(Continued)

(52) U.S. Cl.
CPC .......... *A61B 17/320758* (2013.01); *A61B 2017/00473* (2013.01); *A61B 2017/00876* (2013.01);
(Continued)

(58) Field of Classification Search
CPC ........ A61B 17/3207; A61B 2017/3207; A61B 2017/00876; A61B 2034/731
See application file for complete search history.

(56) References Cited

U.S. PATENT DOCUMENTS

2022/0071654 A1*  3/2022  Jang .............. A61B 17/320758

FOREIGN PATENT DOCUMENTS

DE   10200615162   * 10/2007   ..... A61B 17/320758
JP   2004-016504 A    1/2004
(Continued)

OTHER PUBLICATIONS

International Search Report for PCT/KR2020/019447 dated Apr. 19, 2021.

*Primary Examiner* — Katherine H Schwiker
(74) *Attorney, Agent, or Firm* — Sughrue Mion, PLLC

(57) ABSTRACT

A magnetic catheter is disclosed. The magnetic catheter comprises: a first fixed magnet which is coupled to the front end of a catheter tube; a guide rod of which one end is coupled to the front end of the catheter tube, and the other end protrudes to the front of the catheter tube by a predetermined length; a body which is provided with a drill tip on the front end thereof, and has formed therein an inner space in which the other end of the guide rod is positioned; and a first drive magnet which is coupled to the body along the outer peripheral surface of the body.

8 Claims, 4 Drawing Sheets

(51) Int. Cl.
 *A61B 17/22* (2006.01)
 *A61B 17/32* (2006.01)
 *A61B 34/00* (2016.01)
 *A61M 25/00* (2006.01)
 *A61M 25/01* (2006.01)

(52) U.S. Cl.
 CPC ............ *A61B 2017/22094* (2013.01); *A61B 2017/320056* (2013.01); *A61B 2034/731* (2016.02); *A61M 25/0082* (2013.01); *A61M 25/0127* (2013.01)

(56) References Cited

FOREIGN PATENT DOCUMENTS

| | | | | |
|---|---|---|---|---|
| JP | 5006381 B2 | 8/2012 | | |
| KR | 10-1644551 B1 | 8/2016 | | |
| KR | 10-1659367 B1 | 9/2016 | | |
| KR | 10-1805674 B1 | 12/2017 | | |
| KR | 10-1806081 B1 | 12/2017 | | |
| KR | 10-1818400 B1 | 1/2018 | | |
| KR | 10181400 | * | 1/2018 | ............ A61B 34/30 |
| KR | 10-1831660 B1 | 2/2018 | | |
| KR | 102032674 | * | 10/2019 | ........ A61M 25/0127 |
| WO | 2019/022380 A1 | 1/2019 | | |
| WO | 2019/031678 A1 | 2/2019 | | |

\* cited by examiner

[Fig. 1]
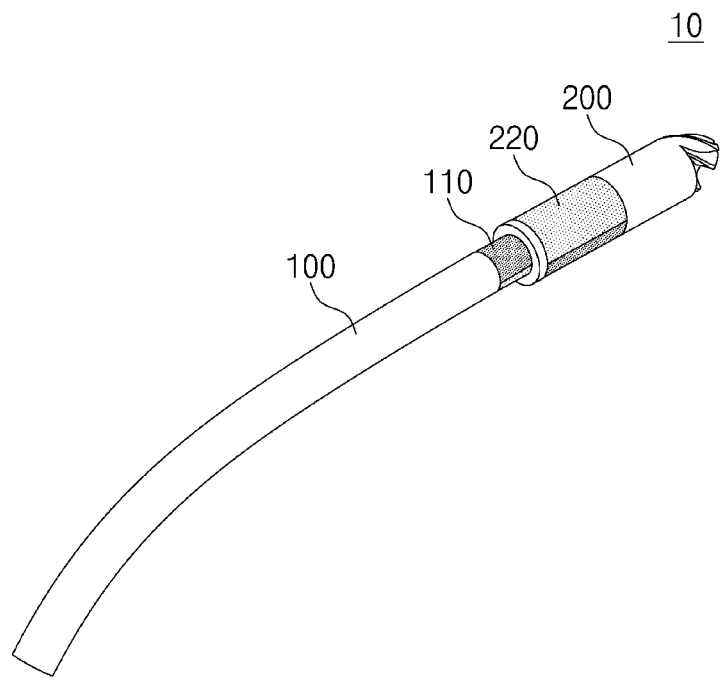
[Fig. 2]
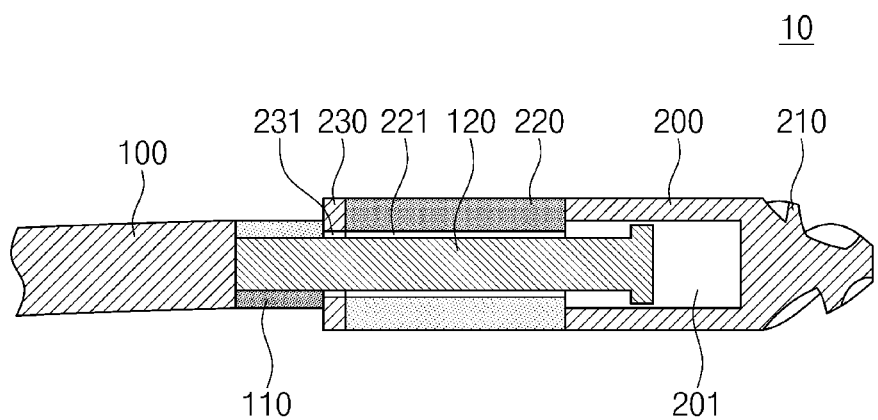

[Fig. 3A]
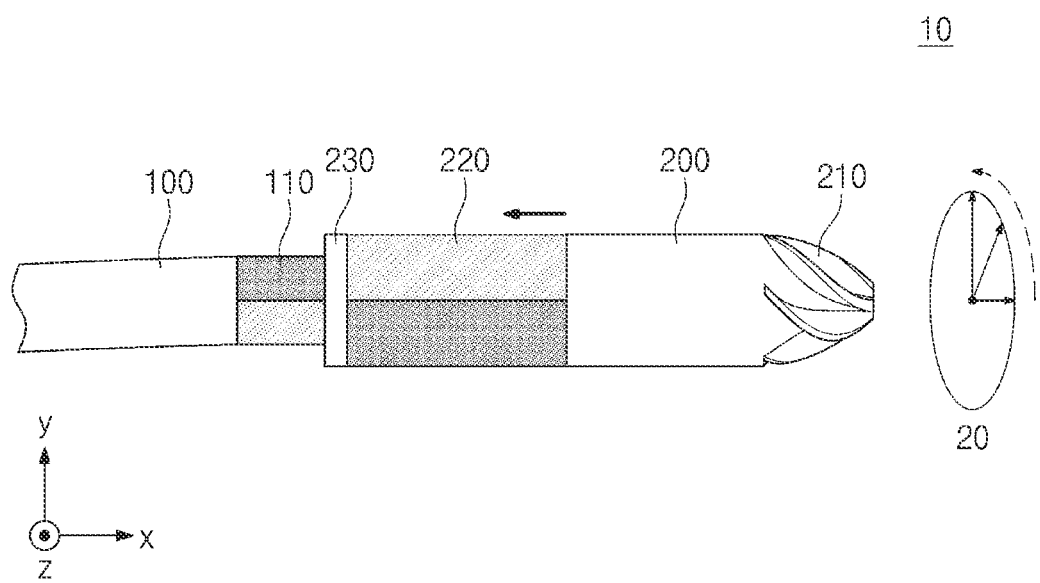
[Fig. 3B]
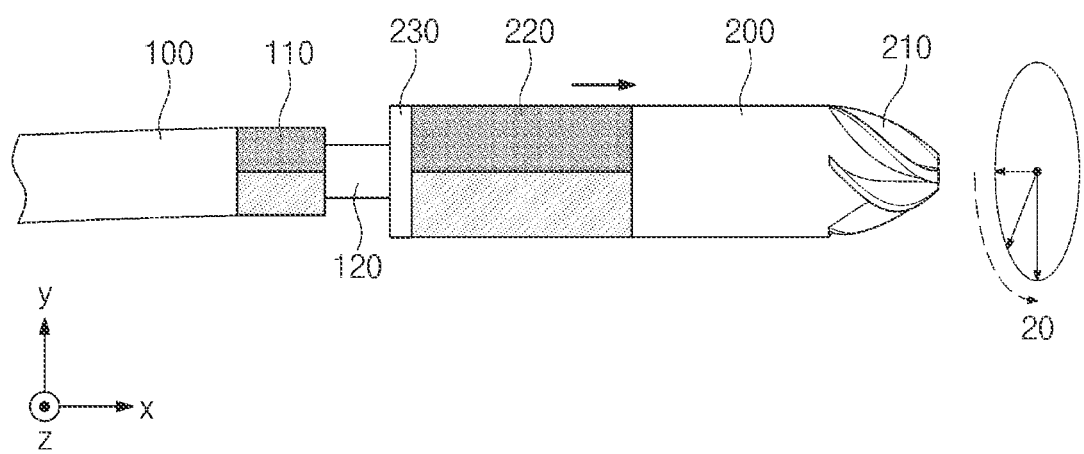

[Fig. 4]
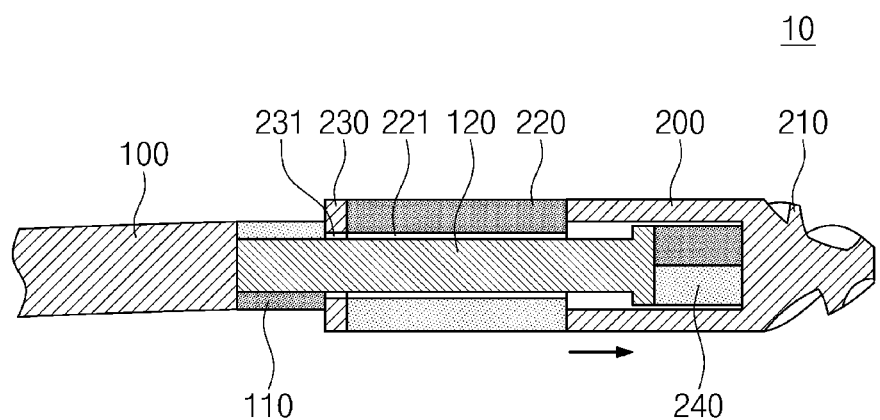
[Fig. 5]
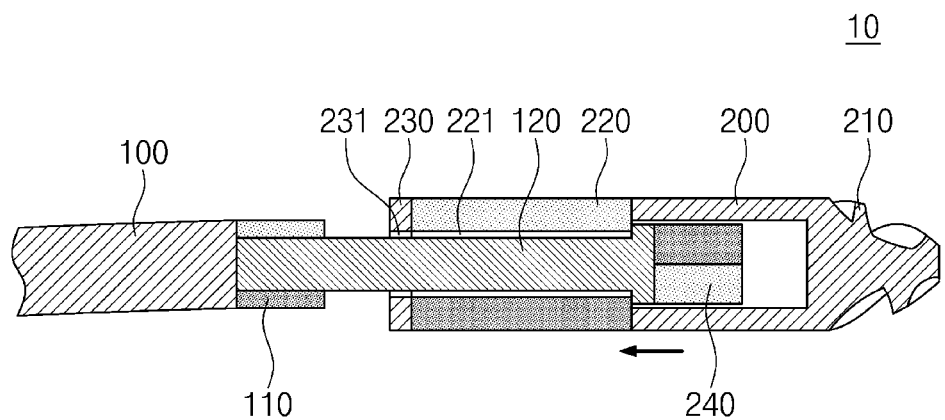

[Fig. 6]
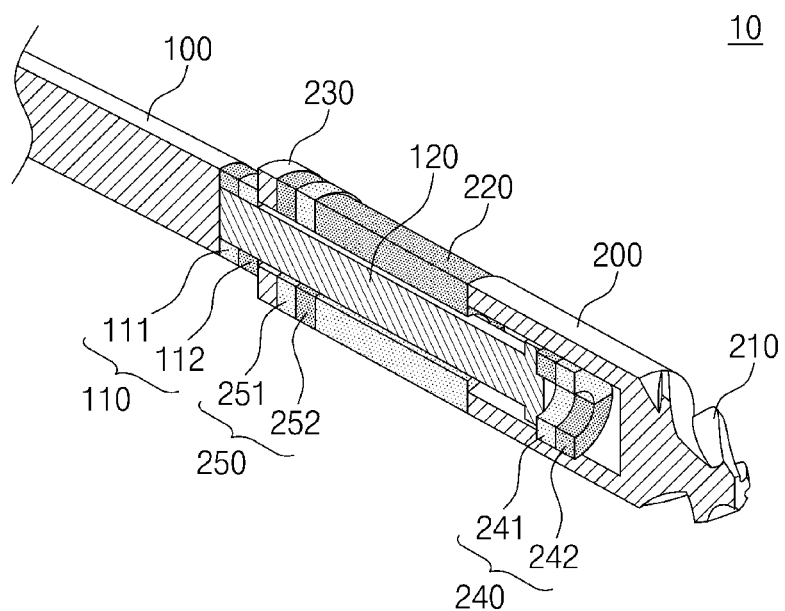
[Fig. 7]
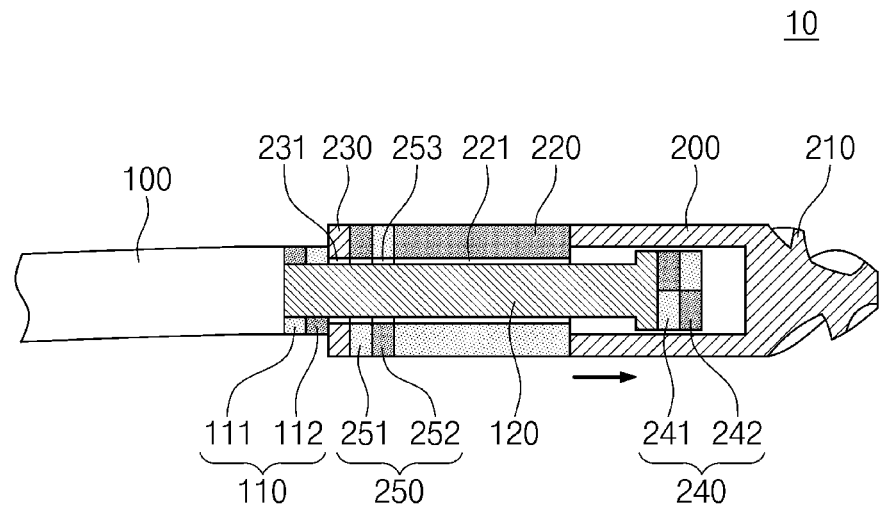

MAGNETIC CATHETER

CROSS REFERENCE TO RELATED APPLICATIONS

This application is a National Stage of International Application No. PCT/KR2020/019447 filed Dec. 30, 2020, claiming priority based on Korean Patent Application No. 10-2020-0011472 filed Jan. 31, 2020 and Korean Patent Application No. 10-2020-0071852 filed Jun. 12, 2020.

TECHNICAL FIELD

The present invention relates to a magnetic catheter, and more particularly, to a magnetic catheter capable of implementing a collision mechanism for improving a tunneling treatment effect.

BACKGROUND ART

A magnetic catheter may be driven by receiving a magnetic torque and a magnetic force by an external magnetic field generated by a magnetic driving system, and may be controlled remotely and precisely, so that the magnetic catheter has been applied to many regions, and research and development of the magnetic catheter has been performed.

Representatively, there is a magnetic catheter applied to a treatment of cardiac arrhythmia, and a magnetic blood vessel treatment catheter for a treatment of blood vessels has been developed. In a case of the magnetic blood vessel treatment catheter, it is very important to perform a tunneling treatment function to break a hard-clogged blood vessel. A conventional magnetic catheter may perform a tunneling treatment such that a person pushes the magnetic catheter by using a hand or a linear slide mechanism on an outer side of a human body while a drill tip rotates.

Such a magnetic catheter has a limitation in that the tunneling treatment may not be effectively performed because a force may not reach an end of the catheter when a lesion is located in a portion after passing through a complex blood vessel.

DISCLOSURE

Technical Problem

The present invention provides a magnetic catheter capable of effectively removing a lesion within a tubular tissue of a human body.

Technical Solution

According to the present invention, a magnetic catheter includes: a catheter tube; a coupling magnet coupled to a front end of the catheter tube; a guide rod having one end coupled to the front end of the catheter tube, and an opposite end protruding forward of the catheter tube by a predetermined length; a body formed therein with an inner space in which the opposite end of the guide rod is located, and provided at a front end thereof with a drill tip; and a drive magnet coupled to the body along an outer peripheral surface of the body.

In addition, the drive magnet included in the magnetic catheter may have a cylindrical shape, and may be bisected into an N-pole and an S-pole based on a central axis of the body.

In addition, the coupling magnet included in the magnetic catheter may have a cylindrical shape, and may be bisected into an N-pole and an S-pole based on a central axis of the catheter tube.

In addition, the magnetic catheter may further include a spacer formed of a non-magnetic material and coupled to a rear end of the body.

In addition, an inner passage may be formed inside the spacer included in the magnetic catheter, and the guide rod may be inserted into the inner passage, in which the opposite end of the guide rod may have a larger diameter than the inner passage.

In addition, the magnetic catheter may further include a fixed magnet located in the inner space, fixedly coupled to the opposite end of the guide rod, and bisected into an N-pole and an S-pole based on a central axis of the guide rod, and the fixed magnet may be arranged such that a polarity of the fixed magnet, which is different from a polarity of the coupling magnet, faces the polarity of the coupling magnet.

In addition, the coupling magnet included in the magnetic catheter may include: a first magnetic layer having a plate shape; and a second magnet layer having a plate shape, coupled to the first magnet layer, and arranged such that a polarity of the second magnet layer, which is different from a polarity of the first magnetic layer, faces the polarity of the first magnetic layer.

In addition, the fixed magnet included in the magnetic catheter may include: a third magnetic layer having a plate shape; and a fourth magnet layer having a plate shape, coupled to the third magnet layer, and arranged such that a polarity of the fourth magnet layer, which is different from a polarity of the third magnetic layer, faces the polarity of the third magnetic layer.

In addition, the magnetic catheter may further include an auxiliary magnet fixedly coupled to the body in a space between the drive magnet and the spacer, and formed therein with a third inner passage, and the auxiliary magnet may include: a fifth magnetic layer having a plate shape; and a sixth magnet layer having a plate shape, coupled to the fifth magnet layer, and arranged such that a polarity of the sixth magnet layer, which is different from a polarity of the fifth magnetic layer, faces the polarity of the fifth magnetic layer.

Advantageous Effects

According to the present invention, the drill tip provided at the front end of the magnetic catheter may rotate and move in forward and rearward directions under the control of an external magnetic field, so that a lesion can be effectively removed by a collision between the drill tip and the lesion.

In addition, according to the present invention, the drill tip may be driven under the control of the external magnetic field, so that a tunneling treatment can be effectively performed even when the magnetic catheter passes through a complex blood vessel.

DESCRIPTION OF DRAWINGS

FIG. 1 is a perspective view showing a magnetic catheter according to one embodiment of the present invention.

FIG. 2 is a sectional view showing the magnetic catheter of FIG. 1.

FIG. 3A and FIG. 3B is a view showing a driving process of the magnetic catheter according to the embodiment of FIG. 1.

FIGS. 4 and 5 are sectional views showing a magnetic catheter according to another embodiment of the present invention.

FIG. 6 is a view showing a magnetic catheter according to still another embodiment of the present invention.

FIG. 7 is a sectional view showing the magnetic catheter according to still another embodiment of the present invention.

BEST MODE

According to the present invention, a magnetic catheter includes: a catheter tube; a coupling magnet coupled to a front end of the catheter tube; a guide rod having one end coupled to the front end of the catheter tube, and an opposite end protruding forward of the catheter tube by a predetermined length; a body formed therein with an inner space in which the opposite end of the guide rod is located, and provided at a front end thereof with a drill tip; and a drive magnet coupled to the body along an outer peripheral surface of the body.

MODE FOR INVENTION

Hereinafter, exemplary embodiments of the present invention will be described in detail with reference to the accompanying drawings. However, the technical idea of the present invention is not limited to the embodiments described herein, but may be realized in different forms. The embodiments introduced herein are provided to sufficiently deliver the idea of the present invention to those skilled in the art so that the disclosed contents may become thorough and complete.

When it is mentioned in the present disclosure that one element is on another element, it means that one element may be directly formed on another element, or a third element may be interposed between one element and another element. Further, in the drawings, thicknesses of films and regions are exaggerated for effective description of the technical contents.

In addition, in various embodiments of the present disclosure, the terms such as first, second, and third are used to describe various elements, but the elements are not limited by the terms. The terms are used only to distinguish one element from another element. Therefore, an element mentioned as a first element in one embodiment may be mentioned as a second element in another embodiment. The embodiments described and illustrated herein include their complementary embodiments. Further, the term "and/or" used herein is used to include at least one of the elements enumerated before and after the term.

As used herein, the terms of a singular form may include plural forms unless the context clearly indicates otherwise. Further, the terms such as "including" and "having" are intended to designate the presence of features, numbers, steps, elements, or combinations thereof described in the present disclosure, and shall not be construed to preclude any possibility of the presence or addition of one or more other features, numbers, steps, elements, or combinations thereof. In addition, the term "connection" used herein is used to include both indirect and direct connection of a plurality of elements.

Further, in the following description of the present invention, detailed descriptions of known functions and configurations incorporated herein will be omitted when they may make the gist of the present invention unnecessarily unclear.

FIG. 1 is a perspective view showing a magnetic catheter according to one embodiment of the present invention, and FIG. 2 is a sectional view showing the magnetic catheter of FIG. 1.

Referring to FIGS. 1 and 2, a magnetic catheter 10 may include a catheter tube 100, a coupling magnet 110, a guide rod 120, a body 200, a drive magnet 220, and a spacer 230.

The catheter tube 100 may have a tube shape having a predetermined length, and may be formed of a flexible material that is deformable. A cross section of the catheter tube 100, which is perpendicular to a longitudinal direction, may have a circular shape, a polygonal shape, or the like. The catheter tube 100 may be formed of a non-magnetic material, and may be inserted into a tubular tissue.

The coupling magnet 110 may be coupled to a front end of the catheter tube 100. The coupling magnet 110 may be a cylindrical magnet, and may be bisected into an N-pole and an S-pole based on a central axis of the catheter tube 100.

The guide rod 120 may have one end coupled to the front end of the catheter tube 100, and an opposite end protruding forward of the catheter tube 100 by a predetermined length. The one end of the guide rod 120 may be inserted into an inner space of the coupling magnet 110. The guide rod 120 may be formed of a non-magnetic material. The guide rod 120 may be inserted into a first inner passage 221 and a second inner passage 231, and the opposite end of the guide rod 120 may be located in the inner space 201. A body part of the guide rod 120 may have a smaller diameter than the first inner passage 221 and the second inner passage 231, and the opposite end of the guide rod 120 may have a larger diameter than the second inner passage 231.

The body 200 may be located on a front side of the coupling magnet 110. The body 200 may have a cylindrical shape having a predetermined diameter, and may be provided at a front end thereof with a drill tip 210. The body 200 may be formed of a non-magnetic material. An inner space 201 may be formed inside the body 200.

The drive magnet 220 may be provided along an outer peripheral surface of the body 200, and may be fixedly coupled to the body 200. The drive magnet 220 may be formed therein with the first inner passage 221, and may have the same diameter as the body 200. The drive magnet 220 may be a cylindrical magnet, and may be bisected into an N-pole and an S-pole based on a central axis of the body 200.

The spacer 230 may have a disc shape having a predetermined thickness, and may be fixedly coupled to a rear end of the body 200. The spacer 230 may be formed of a non-magnetic material. A diameter of the space 230 may be equal to a diameter of the body 200. A second inner passage 231 may be formed in the spacer 230. The spacer 230 may block the drive magnet 220 and the coupling magnet 110 from being directly coupled by a magnetic force.

FIG. 3 is a view showing a driving process of the magnetic catheter according to the embodiment of FIG. 1.

Referring to FIG. 3, a rotating magnetic field 20 may be applied from an outside. The rotating magnetic field 20 may rotate about the central axis of the body 200. According to the present embodiment, an example in which the rotating magnetic field 20 rotates in a counterclockwise direction will be described. FIG. 3(A) shows an operation process of the magnetic catheter 10 while the rotating magnetic field 20 rotates from a −y axis direction to a +y axis direction. FIG. 3(B) shows an operation process of the magnetic catheter 10 while the rotating magnetic field 20 rotates from the +y axis direction to the −y axis direction.

Referring to FIG. 3(A), the drive magnet 220 may be aligned in the +y axis direction according to the rotating magnetic field 20, and in this process, the body 200 may rotate together with the drive magnet 220. The drive magnet 220 aligned in the +y axis direction may be arranged such that a polarity of the drive magnet 220, which is different from a polarity of a fixed magnet 240, faces the polarity of the fixed magnet 240, and an attractive force may be generated between the drive magnet 220 and the fixed magnet 240. Due to the attractive force, the body 200 may move in a −x axis direction along the guide rod 120.

Referring to FIG. 3(B), the drive magnet 220 may be aligned in the −y axis direction according to the rotating magnetic field 20, and in this process, the body 200 may rotate together with the drive magnet 220. The drive magnet 220 aligned in the −y axis direction may be arranged such that the polarity of the drive magnet 220, which is the same as the polarity of the fixed magnet 240, faces the polarity of the fixed magnet 240, and a repulsive force may be generated between the drive magnet 220 and the fixed magnet 240. Due to the repulsive force, the body 200 may move in a +x axis direction along the guide rod 120.

As described above, under the control of the rotating magnetic field 20, the body 200 may moves linearly in forward and rearward directions along the guide rod 120 while rotating according to the rotating magnetic field 20, and in this process, the drill tip 210 provided at the front end of the body 200 may collide with a lesion within a blood vessel. As the rotating magnetic field 20 rotates repeatedly, the drill tip 210 may perform a drilling operation while colliding with the lesion multiple times.

FIGS. 4 and 5 are sectional views showing a magnetic catheter according to another embodiment of the present invention.

Referring to FIGS. 4 and 5, the magnetic catheter 10 may further include a fixed magnet 240. The fixed magnet 240 may be a cylindrical magnet, and may be located in the inner space 201. The fixed magnet 240 may be coupled to the opposite end of the guide rod 120. The fixed magnet 240 may be bisected into an N-pole and an S-pole based on the central axis of the guide rod 120. The fixed magnet 240 may be arranged such that a polarity of the fixed magnet 240, which is different from a polarity of the coupling magnet 110, faces the polarity of the coupling magnet 110.

As described with reference to FIG. 3, when the rotating magnetic field 20 is applied from the outside, the drive magnet 220 and the body 200 may rotate according to the rotating magnetic field 20. In addition, due to the rotation of the drive magnet 220, attractive and repulsive forces may be generated between the drive magnet 220 and the fixed magnet 240.

When the drive magnet 220 is arranged as shown in FIG. 4, an attractive force may be generated between the coupling magnet 110 and the drive magnet 220, and a repulsive force may be generated between the fixed magnet 240 and the drive magnet 220. The repulsive force between the fixed magnet 240 and the drive magnet 220 may increase a linear movement force of the body 200 in the −y axis direction.

When the drive magnet 220 is arranged as shown in FIG. 5, a repulsive force may be generated between the coupling magnet 110 and the drive magnet 220, and an attractive force may be generated between the fixed magnet 240 and the drive magnet 220. The attractive force between the fixed magnet 240 and the drive magnet 220 may increase a linear movement force of the body 200 in the +y axis direction.

As described above, the fixed magnet 240 may be provided to increase a movement force of the body 200 in the forward and rearward directions, so that a collision force of the drill tip 210 with respect to the lesion may be increased.

FIG. 6 is a view showing a magnetic catheter according to still another embodiment of the present invention, and FIG. 7 is a sectional view showing the magnetic catheter according to the embodiment of FIG. 6.

Referring to FIGS. 6 and 7, the coupling magnet 110 may include a first magnet layer 111 and a second magnet layer 112.

The first magnet layer 111 may have a plate shape, and may be bisected into an N-pole and an S-pole based on a central axis thereof.

The second magnet layer 112 may have a plate shape having the same diameter as the first magnet layer 111, and may be bisected into an N-pole and an S-pole based on a central axis thereof. The second magnet layer 112 may be fixedly coupled to the first magnet layer 111, and may be arranged such that a polarity of the second magnet layer 112, which is different from a polarity of the first magnet layer 111, faces the polarity of the first magnet layer 111. The polarity of the second magnet layer 112 may have the same area as the polarity of the first magnet layer 111. Accordingly, a magnetic moment value of the coupling magnet 110 in which the first magnet layer 111 and the second magnet layer 112 are coupled to each other may be zero. In addition, a magnetic field direction of the coupling magnet 110 may be formed in a central axis direction thereof by the above structure.

The fixed magnet 240 may include a third magnet layer 241 and a fourth magnet layer 242.

The third magnet layer 241 may have a plate shape, and may be bisected into an N-pole and an S-pole based on a central axis thereof.

The fourth magnet layer 242 may have a plate shape having the same diameter as the third magnet layer 241, and may be bisected into an N-pole and an S-pole based on a central axis thereof. The fourth magnet layer 242 may be fixedly coupled to the third magnet layer 241, and may be arranged such that a polarity of the fourth magnet layer 242, which is different from a polarity of the third magnet layer 241, faces the polarity of the third magnet layer 241. The polarity of the fourth magnet layer 242 may have the same area as the polarity of the third magnet layer 241. Accordingly, a magnetic moment value of the fixed magnet 240 in which the third magnet layer 241 and the fourth magnet layer 242 are coupled to each other may be zero. In addition, a magnetic field direction of the fixed magnet 240 may be formed in a central axis direction thereof by the above structure.

The magnetic catheter 10 may further include an auxiliary magnet 250. The auxiliary magnet 250 may be located in a space between the drive magnet 220 and the spacer 230, and may be formed therein with a third inner passage 253. The auxiliary magnet 250 may include a fifth magnet layer 251 and a sixth magnet layer 252.

The fifth magnet layer 251 may have a plate shape, and may be bisected into an N-pole and an S-pole based on a central axis thereof.

The sixth magnet layer 252 may have a plate shape having the same diameter as that of the fifth magnet layer 251, and may be bisected into an N-pole and an S-pole based on a central axis thereof. The sixth magnet layer 252 may be fixedly coupled to the fifth magnet layer 251, and may be arranged such that a polarity of the sixth magnet layer 252, which is different from a polarity of the fifth magnet layer 251, faces the polarity of the fifth magnet layer 251. The polarity of the sixth magnet layer 252 may have the same area as the polarity of the fifth magnet layer 251. Accordingly, a magnetic moment value of the auxiliary magnet 250 in which the sixth magnet layer 252 and the fifth magnet layer 251 are coupled to each other may be zero. In addition, a magnetic field direction of the auxiliary magnet 250 may be formed in a central axis direction thereof by the above structure.

The coupling magnet 110, the drive magnet 220, and the auxiliary magnet 250 may be magnetized in the central axis directions thereof due to the above-described arrangements of the magnet layers. When the second magnet layer 112 and the fifth magnet layer 251 are arrange such that the polarity of the second magnet layer 112, which is different from the polarity of the fifth magnet layer 251, faces the polarity of the fifth magnet layer 251, a magnetic field may be generated in a central axis direction of the guide rod 120. A force of the body 200 moving toward the catheter tube 100 in a direction of the magnetic field may be further increased.

When the second magnet layer 112 and the fifth magnet layer 251 are arrange such that the polarity of the second magnet layer 112, which is the same as the polarity of the fifth magnet layer 251, faces the polarity of the fifth magnet layer 251, a magnetic field may be generated in the central axis direction of the guide rod 120. A force of the body 200 moving forward of the catheter tube 100 in the direction of the magnetic field may be further increased.

Although the exemplary embodiments of the present invention have been described in detail above, the scope of the present invention is not limited to a specific embodiment, and should be interpreted by the appended claims. In addition, it should be understood by those of ordinary skill in the art that various changes and modifications can be made without departing from the scope of the present invention.

INDUSTRIAL APPLICABILITY

The magnetic catheter according to the present invention may be used to remove a lesion within a tubular tissue of a human body.

The invention claimed is:

1. A magnetic catheter comprising:
a catheter tube;
a coupling magnet coupled to a front end of the catheter tube;
a guide rod having one end coupled to the front end of the catheter tube, and an opposite end protruding forward of the catheter tube by a predetermined length;
a body having an inner space in which the opposite end of the guide rod is located, and provided at a front end thereof with a drill tip;
a fixed magnet located in the inner space, fixedly coupled to the opposite end of the guide rod, and bisected into an N-pole and an S-pole based on a central axis of the guide rod; and
a drive magnet coupled to the body along an outer peripheral surface of the body and disposed between the coupling magnet and the fixed magnet,
wherein the fixed magnet is arranged such that a polarity of the fixed magnet, which is different from a polarity of the coupling magnet, faces the polarity of the coupling magnet.

2. The magnetic catheter of claim 1, wherein the drive magnet has a cylindrical shape, and is bisected into an N-pole and an S-pole based on a central axis of the body.

3. The magnetic catheter of claim 1, wherein the coupling magnet has a cylindrical shape, and is bisected into an N-pole and an S-pole based on a central axis of the catheter tube.

4. The magnetic catheter of claim 1, further comprising a spacer formed of a non-magnetic material and coupled to a rear end of the body.

5. The magnetic catheter of claim 4, wherein an inner passage is formed inside the spacer, and
the guide rod is inserted into the inner passage, in which the opposite end of the guide rod has a larger diameter than the inner passage.

6. The magnetic catheter of claim 4, further comprising an auxiliary magnet fixedly coupled to the body in a space between the drive magnet and the spacer, and formed therein with a third inner passage,
wherein the auxiliary magnet includes:
a fifth magnetic layer having a plate shape; and
a sixth magnet layer having a plate shape, coupled to the fifth magnet layer, and arranged such that a polarity of the sixth magnet layer, which is different from a polarity of the fifth magnetic layer, faces the polarity of the fifth magnetic layer.

7. The magnetic catheter of claim 1, wherein the coupling magnet includes:
a first magnetic layer having a plate shape; and
a second magnet layer having a plate shape, coupled to the first magnet layer, and arranged such that a polarity of the second magnet layer, which is different from a polarity of the first magnetic layer, faces the polarity of the first magnetic layer.

8. The magnetic catheter of claim 7, wherein the fixed magnet includes:
a third magnetic layer having a plate shape; and
a fourth magnet layer having a plate shape, coupled to the third magnet layer, and arranged such that a polarity of the fourth magnet layer, which is different from a polarity of the third magnetic layer, faces the polarity of the third magnetic layer.

* * * * *